United States Patent [19]

Sunagawa et al.

[11] Patent Number: 5,322,952

[45] Date of Patent: Jun. 21, 1994

[54] PYRROLIDINE DERIVATIVES AND PROCESS FOR PREPARING THE SAME

[75] Inventors: Makoto Sunagawa, Itami; Haruki Matsumura, Nara; Takashi Bando, Osaka, all of Japan

[73] Assignee: Sumitomo Pharmaceuticals Company, Limited, Osaka, Japan

[21] Appl. No.: 2,895

[22] Filed: Jan. 11, 1993

[30] Foreign Application Priority Data

Jan. 10, 1992 [JP] Japan .................................. 4-22104

[51] Int. Cl.$^5$ .......................................... C07D 495/08
[52] U.S. Cl. ................................................. 548/453
[58] Field of Search .................................... 548/543

[56] References Cited

U.S. PATENT DOCUMENTS

| 3,991,076 | 11/1976 | Helsley et al. | 548/453 |
| 4,321,383 | 3/1982 | Sprague | 546/113 |
| 4,608,384 | 8/1986 | Wierzbicki et al. | 548/453 |

FOREIGN PATENT DOCUMENTS

| 0126587 | 11/1984 | European Pat. Off. |
| 0442497 | 8/1991 | European Pat. Off. |
| 3-264586 | 11/1991 | Japan |

OTHER PUBLICATIONS

V. Eswarakrishnan and L. Field, "Sulfinic Acids and Related Compounds. 13. Unsymmetrical . . . and 4(S)-or 4(R)-Mercaptoprolines", *J. Org. Chem.*, vol. 46, No. 21, 1981, pp. 4182-4187.

J. Organic Chemistry, vol. 35, No. 6, 1970, pp. 1924-1927.
J. Organic Chemistry, vol. 46, 1981, pp. 4182-4187.

*Primary Examiner*—David B. Springer
*Attorney, Agent, or Firm*—Sughrue, Mion, Zinn, Macpeak & Seas

[57] ABSTRACT

Pyrrolidine derivatives of the formula (1):

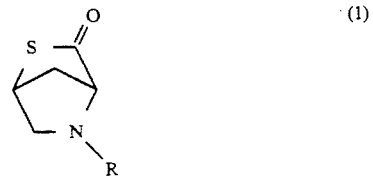

wherein R is a protective group of the amino group, intermediates for constructing the 2-positioned side chain of antibacterial penem and carbapenem compounds, are prepared by allowing

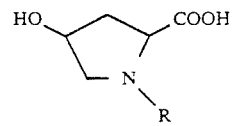

to react with active esterifying agents in the presence of a base, further allowing the product to react with hydrogen sulfide in the presence of a base and then treating the product with a base.

5 Claims, No Drawings

PYRROLIDINE DERIVATIVES AND PROCESS FOR PREPARING THE SAME

This invention relates to pyrrolidine derivatives to be used for constructing the 2-positioned side chain of penem and carbapenem compounds having antibacterial activity, and to a process for preparing the same.

Japanese Patent Publications (Laid-Open) Nos. 19787/1985, 58987/1985, 104088/1985 and which are important intermediates for constructing the 2-positioned side chain of penem and carbapenem compounds known to have excellent antibacterial activity, and represented by the following formula (5):

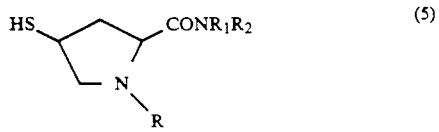

wherein R represents a protective group for the amino group, and $R_1$ and $R_2$ represent, independently, any of
(a) a hydrogen atom;
(b) a substituted or unsubstituted lower alkyl, alkenyl or alkynyl group;
(c) a substituted or unsubstituted cycloalkyl, cycloalkylalkyl, cycloalkylalkenyl or cycloalkylalkynyl group;
(d) a substituted or unsubstituted aralkyl, aralkenyl or aralkynyl group; and
(e) a substituted or unsubstituted heteroaralkyl, heteroaralkenyl, heteroaralkynyl, heterocyclyl, heterocyclylalkyl, heterocyclylalkenyl or heterocyclylalkynyl group;

or $R_1$ and $R_2$ are an alkylene chain linked each other or an alkylene chain containing an oxygen, sulfur or substituted nitrogen atom, to form a cyclic amino group of 4–8 membered ring together with the adjacent nitrogen atom.

These derivatives are conventionally prepared by that a thio ester compound which is derived from 4-hydroxyproline and represented by the following formula (6):

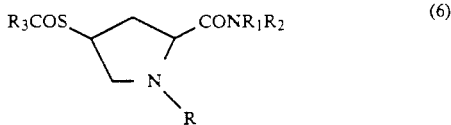

wherein R, $R_1$ and $R_2$ have the same meanings as above and $R_3$ represents a lower alkyl or aryl group, is subjected to hydrolysis or solvolysis with an alkali metal base. This method, however, is not satisfactory from a viewpoint of commercial production, because a relatively expensive alkali thiocarbonate is required as a material for preparing a thio ester compound of the formula (6), and some by-products are readily formed during the course of preparation.

Journal of Organic Chemistry, 46, 4182–4187 (1981) and Bulletin of Pharmaceutical Chemistry, 20, 543–549 (1972) report a method for converting trans-4-hydroxy-L-proline to a thiolactone of the following formula (7):

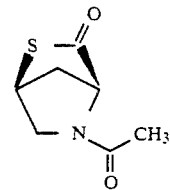

This thiolactone, however, is not a favorable intermediate for preparing penem and carbapenem antibacterial agents, because the acetyl group is not necessarily be eliminated efficiently under moderate conditions. Furthermore, thiolactone syntheses described in these literatures are not satisfactory for commercial production from the viewpoints of number of steps and yield.

After extensive studies to dissolve these problems, the present inventors have found that a pyrrolidine derivative represented by the formula (1):

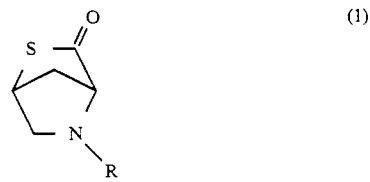

in which R has the same meaning as above, is readily derived from 4-hydroxyproline and that a treatment of the compound (1) with amines results in a 4-mercaptopyrrolidine derivative represented by the following formula (5):

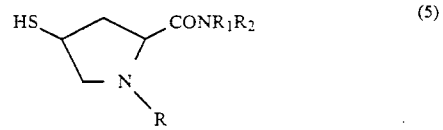

wherein R, $R_1$ and $R_2$ have the same meanings as above.

According to the present invention, a pyrrolidine derivative represented by the formula (1) as mentioned above; is provided. In addition, a process for preparing pyrrolidine derivatives of the formula (1) mentioned above, is provided wherein (A) a compound represented by the following formula (2):

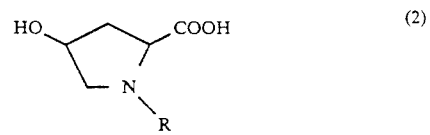

in which R has the same meaning as above, is allowed to react with an active esterifying agent in the presence of a base, and then the product is allowed to react with hydrogen sulfide in the presence of a base, to give a compound represented by the following formula (3):

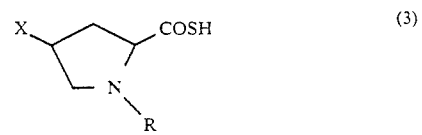

in which R has the same meaning as above and X means an active ester group of a hydroxyl group, and further the product (3) is treated with a base. Alternatively, (B) the compound of the formula (2) mentioned above is allowed to react with an active esterifying agent in the presence of a base, and then the product is allowed to react with an alkali metal salt of hydrogen sulfide. Furthermore, a process for preparing 4-mercaptopyrrolidine derivatives represented by the formula (5) mentioned above is provided by allowing the pyrrolidine derivative represented by the formula (1) mentioned above to react with an amine compound represented by the following formula (4):

HNR$_1$R$_2$  (4)

in which R$_1$ and R$_2$ have the same meanings as above, or mineral acid salts thereof.

The compound (1) of the present invention, and processes for preparing the same, as well as a process for preparing 4-mercaptopyrrolidine derivatives of the formula (5) mentioned above, from the present compounds, said (5) being important intermediates, are explained hereinunder.

Definitions of the various groups in the present invention will be referred to hereinafter.

As for R representing a protective group for the amino group, mention is made of
(i) substituted and unsubstituted C$_{1-6}$ lower alkoxycarbonyl groups;
(ii) substituted and unsubstituted C$_{2-6}$ lower alkenyloxycarbonyl groups;
(iii) substituted and unsubstituted benzyloxycarbonyl groups;
(iv) substituted and unsubstituted benzyl groups; or
(v) substituted and unsubstituted trialkylsilyl, dialkylarylsilyl, alkyldiarylsilyl and triarylsilyl groups.

Substituents may be selected from one or more C$_{1-4}$ lower alkyl groups, C$_{1-4}$ lower alkoxy groups, aryl groups, halogen atoms and nitro groups.

The substituted and unsubstituted C$_{1-6}$ lower alkoxycarbonyl groups are, for example, methoxycarbonyl, tert-butyloxycarbonyl, 2-iodoethyloxycarbonyl, 2-bromoethyloxycarbonyl, 1,1-dimethyl-2-iodoethyloxycarbonyl and 2,2,2-trichloroethyloxycarbonyl.

The substituted and unsubstituted C$_{2-6}$ lower alkenyloxycarbonyl groups are, for example, vinyloxycarbonyl, allyloxycarbonyl, 2-chloroallyloxycarbonyl and cinnamyloxycarbonyl.

The substituted and unsubstituted benzyloxycarbonyl groups are, for example, benzyloxycarbonyl, p-nitrobenzyloxycarbonyl, p-methoxybenzyloxycarbonyl, p-chlorobenzyloxycarbonyl and 2,4,6-trimethylbenzyloxycarbonyl.

The substituted and unsubstituted benzyl groups are, for example, benzyl, p-nitrobenzyl, p-methoxybenzyl, p-chlorobenzyl, triphenylmethyl and bis(p-methoxyphenyl)methyl.

The substituted and unsubstituted trialkylsilyl, dialkylarylsilyl, alkyldiarylsilyl and triarylsilyl groups are, for example, trimethylsilyl, triethylsilyl, triisopropylsilyl, tert-butyldimethylsilyl, tert-butyldiphenylsilyl, diphenylmethylsilyl and triphenylsilyl.

R is preferably a substituted or unsubstituted C$_{2-6}$ lower alkenyloxycarbonyl group or a substituted or unsubstituted benzyloxycarbonyl group.

R$_1$ and R$_2$ each is substituted or unsubstituted lower alkyl, lower alkenyl, or lower alkynyl groups having 1-6 carbon atoms, respectively, for example, methyl, ethyl, n-propyl, isopropyl, n-butyl, 2-propenyl, 2-butenyl, ethynyl, 2-butynyl, 2-hydroxyethyl, 3-chloroethyl, 2-methoxyethyl, 3-pentenyl, 4-hexynyl.

The substituted or unsubstituted cycloalkyl, cycloalkylalkyl, cycloalkylalkenyl, or cycloalkylalkynyl groups are those having 3-6 carbon atoms in the cycloalkyl ring and 1-6 carbon atoms in the alkyl, alkenyl or alkynyl portion, for example, cyclopentyl, cyclohexyl, 2-cyclobutylethyl, 6-cyclohexylhexyl, 2-(4-methoxycyclohexyl)ethyl, 5-(3-bromocyclopentyl)pentyl, 5-(cyclopentyl)-4-pentenyl and 6-(cyclohexyl)-3-hexynyl.

The substituted or unsubstituted aralkyl, aralkenyl or aralkynyl group are those having a substituted or unsubstituted phenyl group as the aryl portion and having 1-3 carbon atoms as the alkyl, alkenyl or alkynyl portion, for example, benzyl, p-nitrobenzyl, 2-chlorobenzyl, 2-phenylethyl, cinnamyl and 3-cyclopentyl-2-propynyl.

The substituted or unsubstituted heteroaralkyl, heteroaralkenyl, heteroaralkynyl, heterocyclyl, heterocyclylalkyl, heterocyclylalkenyl, or heterocyclylalkynyl group are groups having one or more hetero atoms selected from 1-4 oxygen, nitrogen, and sulfur atoms and having 1-6 carbon atoms in the alkyl, alkenyl or alkynyl portion linked to the heterocyclic portion, for example, 2-, 3- and 4-pyridyl-lower alkyl, 2-, 4- and 5-pyrimidyl-lower alkyl, 3-(2-pyridyl)-2-propenyl, 4-(3-pyridyl)-2-butynyl, N-methyl-2-, -3- or -4-piperidino, N-propyl-2- or -3-morpholino, N-methyl-2- or -3-thiomorpholino, N-ethyl-2-, -3- or -4-piperidino-lower alkyl, N-propyl-2- or -3-morpholino-lower alkyl, N-methyl-2- or -3-thiomorpholino- lower alkyl, 6-(N-methyl-2-piperidino)-3-hexenyl and 6-(N-methyl-2-piperidino)-3-hexynyl.

R$_1$ and R$_2$ which are an alkylene chain linked each other or an alkylene chain containing oxygen, sulfur or substituted nitrogen atom to form a cyclic amino group of 4-8 membered ring together with the adjacent nitrogen atom, are, for example, azetidino, 2-methylazetidino, pyrrolidino, 3-oxopyrrolidino, piperidino, 4-oxopiperidino, morpholino, thiomorpholino, 4-methylpiperazino, 4-propylpiperazino, 4-(2-hydroxyethyl)piperazino, 4-(2-methoxyethyl)piperazino, 4-(4-propoxybutyl)piperazino, 4-(N,N-dimethylcarbamoylmethyl)piperazino, 4-(allyloxycarbonylmethyl)piperazino, 4-(benzyloxycarbonylmethyl)piperazino, 4-(N,N-dimethylcarbamoyloxyethyl)piperazino, 4-methyl-1,4-diaza-1-cycloheptyl, 4-(2-methoxyethyl)-1,4-diaza-1-cycloheptyl, 4-(N,N-dimethylcarbamoylmethyl)-1,4-diaza-1-cycloheptyl, 4-(benzyloxycarbonylmethyl)-1,4-diaza-1-cycloheptyl, 4-(2-carbamoyloxyethyl)-1,4-diaza-1-cycloheptyl, 5-methyl-1,5-diaza-1-cyclooctyl, 5-(2-methoxyethyl)-1,5-diaza-1-cyclooctyl, 5-(N,N-dimethylcarbamoylmethyl)-1,5-diaza-1-cyclooctyl and 5-(benzyloxycarbonylmethyl)-1,5-diaza-1-cyclooctyl.

One or more substituents in R$_1$ and R$_2$ may be selected independently from carboxyl, sulfo, C$_{1-6}$ lower alkyl, C$_{1-6}$ lower alkoxyl, C$_{1-6}$ lower alkoxycarbonyl, optionally substituted benzyloxycarbonyl groups, halogen atoms, hydroxyl, cyano, nitro, amino, mono(C$_{1-4}$)-alkylamino, C$_{1-6}$ alkylthio, C$_{1-6}$ alkylsulfinyl, C$_{1-6}$ alkylsulfonyl, carbamoyl optionally substituted with one or two C$_{1-4}$ lower alkyl groups, and lower alkyl groups substituted with any of the substituents as mentioned above. Preferences of R$_1$ and R$_2$ are independently each a hydrogen atom, a lower alkyl group which may be substituted, an aralkyl group which may be substituted or a heteroaralkyl group which may be substituted or $R_1$ and $R_2$ link each other to form an alkylene chain or are an alkylene chain containing an oxygen, sulfur or substituted nitrogen atom, and form a cyclic amino group of 4-8 membered ring together with the adjacent nitrogen atom.

The mineral acid salts of the amine compound represented by the formula (4) mentioned above are, for example, hydrohalides such as hydrochloride, hydrobromide and hydrofluoride, perhalates such as perchlorate and periodate, sulfate, phosphate, acetate, oxalate and sulfonates such as benzenesulfonate.

The active ester group for the hydroxyl and carboxyl groups represented by X, are, for example, halogen atoms such as chlorine, bromine and iodine, lower alkylsulfonyloxy groups such as methanesulfonyloxy and ethanesulfonyloxy groups, trihaloalkylsulfonyloxy groups such as trifluoromethanesulfonyloxy group, and arylsulfonyloxy groups such as benzenesulfonyloxy and p-toluenesulfonyloxy groups. Preferences are a lower alkylsulfonyloxy group and an arylsulfonyloxy group.

Pyrrolidine derivatives of the formula (1) have stereoisomers due to asymmetric carbons located at their 1- and 4-positions. Simialrly, 4-mercaptopyrrolidine derivaties of the formula (5) have stereoisomers due to asymmetric carbons located at their 2- and 4-positions. These isomers are conveniently set forth here in the form of single plane formula. Needless to say, the present invention includes all these isomers. However, preferable intermediates for penem and carbapenem compounds are those having [1S,4S] and [1R,4R] configurations for compound (1) and those having [2S,4S] and [2R,4R] configurations for compound (5).

Process for preparing compounds (1) of the present invention, as well as process for preparing 4-mercaptopyrrolidine derivatives of the formula (5), which are important intermediates, from compound (1), will be explained in detail hereinafter.

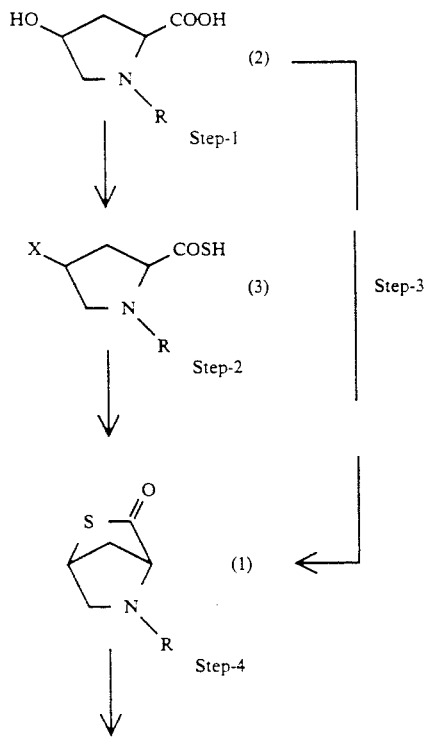

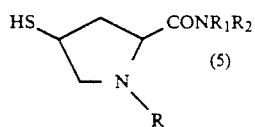

[In the formulae, R, $R_1$, $R_2$ and X have the same meanings as above.]

(1) Step-1

Compound (3) is prepared by allowing compound (2) to react with an active esterifying agent in the presence of a base, and then with hydrogen sulfide in the presence of a base. This step-1 consists of active esterification of carboxylic acid portion, active esterification of hydroxyl group portion and a reaction with hydrogen sulfide. These steps are usually conducted in series according to the order mentioned above.

The bases used in these reactions are, for example, trialkylamines such as triethylamine and diisopropylethylamine, pyridine compounds such as pyridine, lutidine and picoline, quinoline, imidazole, N-methylpyrrolidine, 1,5-diazabicyclo[4.3.0]non-5-ene, 1,4-diazabicyclo[2.2.2]octane and 1,8-diazabicyclo[5.4.0]-undec-7-ene. Preference is a trialkylamines.

The active esterifying agents are, for example, sulfonyl halides such as methanesulfonyl chloride, benzenesulfonyl chloride and toluenesulfonyl chloride, sulfonic acid anhydrides such as methanesulfonic acid anhydride and toluenesulfonic acid anhydride, alkyl chlorocarbonates such as ethyl chlorocarbonate, isopropyl chlorocarbonate and sec-butyl chlorocarbonate, oxalyl chloride, thionyl chloride, phosphorus oxychloride and phosphorus trichloride. The active esterification agents of carboxylic acid portion and active esterifying agents of hydroxyl group portion may be the same or different. Preferences are alkyl chlorocarbonates, alkylsulfonic acid chlorides and arylsulfonic acid chlorides as active esterifying agents of carboxylic acid portion and alkylsulfonic acid chlorides and arylsulfonic acid chlorides as the active esterifying agents of hydroxyl group portion.

Reaction may be carried out in a conventional solvent which does not exert adverse effects, for example, ethers such as dioxane, diethyl ether and tetrahydrofuran, and halogenated hydrocarbons such as methylene chloride, chloroform and 1,2-dichloroethane. Reaction temperature is not limitative, but the reaction is usually carried out under cooling or heating. Halogenated hydrocarbons are preferable solvents. The preferred reaction temperature is from $-50°$ C. to room temperature.

The reaction with hydrogen sulfide is preferably carried out without once isolation of the intermediate compound produced above. The reaction with hydrogen sulfide is desirably conducted in the presence of bases. Although the reaction is effected at any temperature, it is usually conducted under cooling or heating, preferably in the range of $-50°$ C. to room temperature.

Amount of reagents used in this step is preferably enough equivalent to proceed with the reaction. Preferences are 1-3 equivalents of bases for active esterification of carboxylic acid potion, 1-3 equivalents of bases for active esterification of hydroxyl group portion and 1-3 equivalents of bases for reaction with hydrogen sulfide. Amounts of esterifying agents are preferably 1-2 equivalents for esterification of carboxylic acid portion and 1–2 equivalents for esterification of hydroxyl group portion. Hydrogen sulfide is used in amount of preferably 1–2 equivalents, but may be larger than 2 equivalents.

For example, (2S,4R)-1-p-nitrobenzyloxycarbonyl-4-hydroxy-2-pyrrolidinecarboxylic acid is allowed to react with triethylamine and methanesulfonyl chloride in methylene chloride, and then with hydrogen sulfide, thereby to give (2S,4R)-1-p-nitrobenzyloxycarbonyl-4-methanesulfonyloxy-2-pyrrolidinethiocarbonic acid.

(2) Step-2

Compound (1) is prepared by treating compound (3) with a base.

The base used in this reaction is, for example, alkali metal hydrides such as sodium hydride and potassium hydride, alkali metal hydroxides such as sodium hydroxide and potassium hydroxide, alkali metal carbonates such as sodium carbonate and potassium carbonate, alkali metal hydrogencarbonates such as sodium hydrogencarbonate and potassium hydrogencarbonate, alkali metal phosphates such as disodium hydrogenphosphate, dipotassium hydrogenphosphate, trisodium phosphate and tripotassium phosphate, trialkylamines such as triethylamine and diisopropylethylamine, pyridine compounds such as pyridine, lutidine and picoline, quinoline, imidazole, N-methylpyrrolidine, 1,5-diazabicyclo[4.3.0]non-5-ene, 1,4-diazabicyclo[2.2.2]-octane and 1,8-diazabicyclo[5.4.0]undec-7-ene. Trialkylamines and pyridines are preferable. Amount of bases is enough to proceed with the reaction, preferably 1–3 equivalents.

Reaction may be carried out in a conventional solvent or mixed solvent which does not exert adverse effects, for example, ethers such as dioxane, diethyl ether and tetrahydrofuran, halogenated hydrocarbons such as methylene chloride, chloroform and 1,2-dichloroethane, aromatic hydrocarbons such as benzene, toluene, xylene and chlorobenzene, non-protonic polar solvents such as acetonitrile, N,N-dimethylformamide, N,N-dimethylacetamide and sulfolane, and acetates such as ethyl acetate. Preferences are halogenated hydrocarbons and ethers.

Reaction temperature is not limitative, but the reaction is preferably carried out at a temperature within the range from room to refluxing temperatures, preferably 10°–80° C.

For example, (2S,4R)-1-p-nitrobenzyloxycarbonyl-4-methanesulfonyl-2-pyrrolidinethiocarboxylic acid is allowed to react with disodium hydrogenphosphate or triethylamine in methylene chloride or tetrahydrofuran, thereby to give (1S,4S)-5-p-nitrobenzyloxycarbonyl-2-thia-5-azabicyclo[2.2.1]heptan-3-one.

(3) Step-3

Compound (1) is prepared by allowing compound (2) to react with an active esterifying agent in the presence of a base, and then with alkali metal salts of hydrogen sulfide.

This reaction may be carried out in the same way as that described in Step-1. The alkali metal salts of hydrogen sulfide used are, for example, sodium sulfide, potassium sulfide and sodium sulfhydrate. The alkyl metal salts of hydrogen sulfide should be enough to proceed with the reaction, preferably 1–3 equivalents.

Specifically, following compounds are obtained by processes through Steps-1 and -2, or through Step-3:
(1S,4S)-5-(2,2,2-trichloroethyloxycarbonyl)-2-thia-5-azabicyclo[2.2.1]hepan-3-one;
(1S,4S)-5-tert-butyloxycarbonyl-2-thia-5-azabicyclo[2.2.1]-heptan-3-one;
(1S,4S)-5-benzyloxycarbonyl-2-thia-5-azabicyclo[2.2.1]-heptan-3-one;
(1S,4S)-5-p-nitrobenzyloxycarbonyl-2-thia-5-azabiclo[2.2.1]-heptan-3-one;
(1S,4S)-5-p-chlorobenzyloxycarbonyl-2-thia-5-azabicyclo[2.2.1]heptan-3-one;
(1S,4S)-5-p-methoxybenzyloxycarbonyl-2-thia-5-azabicyclo[2.2.1]heptan-3-one;
(1S,4S)-5-allyloxycarbonyl-2-thia-5-azabicyclo[2.2.1]heptan-3-one;
(1S,4S)-5-crotyloxycarbonyl-2-thia-5-azabicyclo[2.2.1]heptan-3-one.

(4) Step-4

Compound (5) is prepared by allowing compound (1) to react with an amine compound represented by the formula (4) mentioned above or mineral acid salts thereof in the presence or absence of a base. No bases are necessary when the amine compound (4) is in the free form. The presence of bases is preferable when mineral acid salts are used.

The base used in this reaction is, for example, alkali metal hydrides such as sodium hydride and potassium hydride, alkali metal hydroxides such as sodium hydroxide and potassium hydroxide, alkali metal carbonates such as sodium carbonate and potassium carbonate, alkali metal hydrogencarbonate such as sodium hydrogencarbonate and potassium hydrogencarbonate, trialkylamides such as triethylamine and diisopropylethylamine, pyridine compounds such as pyridine, lutidine and picoline, quinoline, N-methylpyrrolidine, 1,5diazabicyclo[4.3.0]non-5-ene, 1,4-diazabicyclo[2.2.2]octane, 1,8-diazabicyclo[5.4.0]undec-7-ene and n-butyllithium. Preference bases are trialkylamines and pyridines.

Reaction may be carried out in a conventional solvent which does not exert adverse effects, for example, ethers such as dioxane, diethyl ether and tetrahydrofuran, halogenated hydrocarbons such as methylene chloride, chloroform and 1,2-dichloroethane, aromatic hydrocarbons such as benzene, toluene, xylene and chlorobenzene, non-protonic polar solvents such as acetonitrile, N,N-dimethylformamide, N,N-dimethylacetamide and sulfolane, and acetate esters such as ethyl acetate. The solvent may be mixed with alcohols such as methanol and ethanol. The reaction is effected in the presence or absence of water.

Reaction temperature is not limitative, but the reaction is usually carried out under cooling or heating, preferably at a temperature ranging from 0° to 100° C., more preferably from 0° to 40° C.

For example, (1S,4S)-5-p-nitrobenzyloxycarbonyl-2-thia-5-azabicyclo[2.2.1]heptan-3-one is allowed to react with 1-(2-methoxyethyl)-piperazine or N-methyl-N-(3-pyridylpropyl)amine in benzene or tetrahydrofuran to give each corresponding 4-mercaptopyrrolidine derivative.

Specifically, the following compounds are obtained by the process through Step-4 mentioned above:
(2S,4S)-N,N-dimethyl-1-allyloxycarbonyl-4-mercapto-2-pyrrolidinecarboxamide;
(2S,4S)-N-(2-phenylethyl)-1-benzyloxycarbonyl-4-mercapto-2-pyrrolidinecarboxamide;
(2S,4S)-N-(3-pyridylethyl)-1-benzyloxycarbonyl-4-mercapto-2-pyroolidinecarboxyamide;
(2S,4S)-N-methyl-N-(4-pyridylethyl)-1-benzyloxycarbonyl-4-mercapto-2-pyrrolidinecarboxamide;

(2S,4S)-N-(2-hydroxyethyl)-N-(2-pyridylmethyl)-1-allyloxycarbonyl-4-mercapto-2-pyrrolidinecarboxamide;

1-[2S,4S)-1-allyloxycarbonyl-4-mercapto-2-pyrrolidinecarbonyl]-pyrrolidine;

1-[(2S,4S)-1-allyloxycarbonyl-4-mercapto-2-pyrrolidinecarbonyl]-4-methylpiperidine;

1-[(2S,4S)-1-allyloxycarbonyl-4-mercapto-2-pyrrolidine-carbonyl]-morpholine;

1-[(2S,4S)-1-nitrobenzyloxycarbonyl-4-mercapto-2-pyrrolidinecarbonyl]-4-methylpiperazine;

1-[(2S,4S)-1-allyloxycarbonyl-4-mercapto-2-pyrrolidinecarbonyl]-4-(2-hydroxyethyl)piperazine;

1-[(2S,4S)-1-allyloxycarbonyl-4-mercapto-2-pyrrolidinecarbonyl]-4-(2-methoxyethyl)piperazine;

1-[(2S,4S)-1-p-nitrobenzyloxycarbonyl-4-mercapto-2-pyrrolidinecarbonyl]-4-(N,N-dimethylcarbamoylmethyl)piperazine;

1-[(2S,4S)-1-allyloxycarbonyl-4-mercapto-2-pyrrolidinecarbonyl]-4-(allyloxycarbonylmethyl)piperazine;

1-[(2S,4S)-1-allyloxycarbonyl-4-mercapto-2-pyrrolidinecarbonyl]-4-(benzyloxycarbonylmethyl)piperazine;

1-[(2S,4S)-1-allyloxycarbonyl-4-mercapto-2-pyrrolidinecarbonyl]-4-[2-(N,N-dimethylcarbamoyloxy)ethyl]-1,4-diazacycloheptane; and 1-[(2S,4S)-1-allyloxycarbonyl-4-mercapto-2-pyrrolidinecarbonyl]-5-methyl-1,5-diazacyclooctane.

Compounds (3), (1) and (5) resulting from Steps 1-4 mentioned above can be employed for each subsequent step after evaporating solvent without any further purification. If desired, they may be isolated and purified through distillation, crystallization, chromatography, etc.

The present invention makes it possible to commercially prepare 4-mercaptopyrrolidine derivatives which are important intermediates for constructing the 2-positioned side chain portion of penem and carbapenem compounds known to have excellent antibacterial activity.

The present invention will more specifically be explained by referring to the following Examples and Reference Example, which are, however, never construed to be limitative.

EXAMPLE 1-(1)

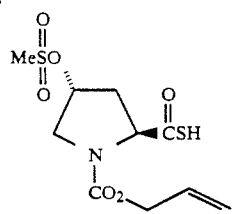

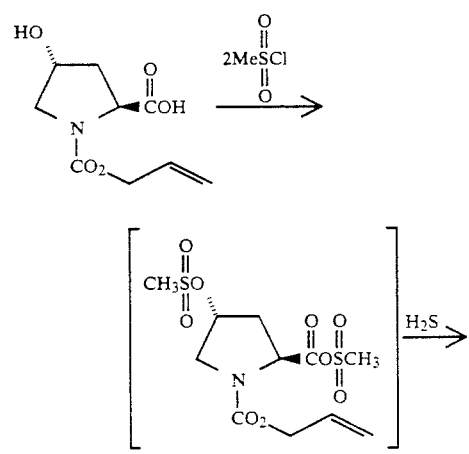

-continued

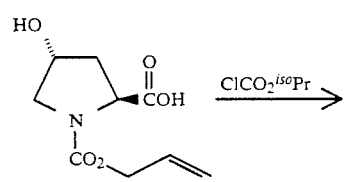

To a solution of (2S,4R)-1-allyloxycarbonyl-4-hydroxy-2-pyrrolidinecarboxylic acid (221 mg) in methylene chloride (3 ml) cooled to 0° C., were added triethylamine (260 mg) and methanesulfonyl chloride (270 mg). The mixture was stirred at 0° C. for 30 minutes. Triethylamine (256 mg) was added thereto, and an excessive amount of hydrogen sulfide was passed through the mixture for 30 minutes. After concentrated hydrochloric acid (208 mg) was added, the mixture was diluted with ethyl acetate (15 ml) and dried over magnesium sulfate. Distillation of the solvent gate (2S,4R)-1-allyloxycarbonyl-4-methanesulfonyloxy-2-pyrrolidinethiocarboxylic acid.

IR (neat): 1700 cm$^{-1}$

NMR(CDCl$_3$) δ2.35(1H, m), 2.70(1H, m), 3.06(3H, m), 3.77(1H, m), 4.00(1H, m), 4.50-4.73(3H, m), 5.14-5.39(3H, m), 5.90(1H, m)

EXAMPLE 1-(2)

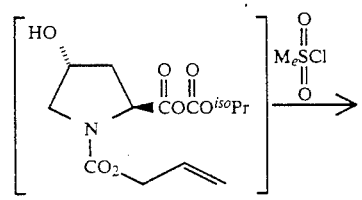

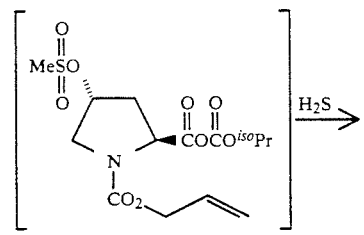

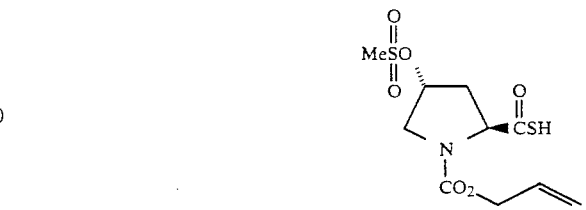

To a solution of (2R,4R)-1-allyloxycarbonyl-4-hydroxy-2-pyrrolidinecarboxylic acid (559 mg) in methylene chloride (15ml), cooled to −10° C., were added triethylamine (329 mg) and isopropyl chlorocarbonate (366 mg). The mixture was stirred at −10° C. for 20 minutes. Triethylamine (329 mg) and methanesulfonyl chloride (342 mg) were added thereto, and the mixture was stirred at −10° C. for 20 minutes. After triethylamine (657 mg) was added, an excessive amount of hydrogen sulfide was passed through for 30 minutes. Concentrated hydrochloric acid (790 mg) and ethyl acetate (20 ml) were added thereto, and the mixture was dried above magnesium sulfate. After a substance left undissolved was separated by filtration, the solvent was removed by vacuum distillation, thereby to give oily crude (2S,4R)-1-allyloxycarbonyl-4-methanesulfonyloxy -2-pyrrolidinethiocarboxylic acid (800 mg). This compound was mixed with 1N-sodium hydroxide solution (4 ml) and toluene (4 ml). Liquid layers were separated and the aqueous layer was further washed with toluene (3 ml). Aqueous layer was acidified with 1N-hydrochloric acid (5 ml) and extracted with ethyl acetate (10 ml) and again with ethyl acetate (5 ml). Organic layers were combined and dried over magnesium sulfate. Distillation of the solvent gave (2S,4R)-1-allyloxycarbonyl-4-methanesulfonyloxy-2-pyrrolidinethiocarboxylic acid.

EXAMPLE-2

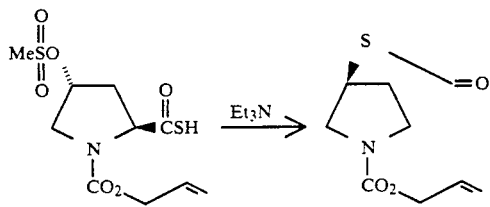

To a solution of (2S,4R)-1-allyloxycarbonyl-4-methanesulfonyloxy-2-pyrrolidine-thiocarboxylic acid (45.7 mg) in methylene chloride (1 ml), was added triethylamine (74.7 mg). The mixture was stirred at 50° C. for 6 hours. After the reaction was over, the solvent was distilled off. After 1N-hydrochloric acid (1 ml) and water (2 ml) were added, the mixture was extracted with ethyl acetate (5 ml), and the extract was dried over magnesium sulfate. Distillation of the solvent, followed by purification of the residue by silica gel chromatography, gate (1S,4S)-5-allyloxycarbonyl-2-thia-5-azabicyclo[2.2.1]heptan-3-one.

IR (neat): 1716 cm$^{-1}$
NMR(CDCl$_3$) δ2.18(2H, m), 3.65(1H, m), 3.85(1H, dd, J=3, 10 Hz), 4.14(1H, m), 4.63(2H, d, J=5 Hz), 4.67(1H, m), 5.22(1H, d, J=10 Hz), 5.32(1H, d, J=17 Hz), 5.92(1H, tdd, J=5, 10, 17 Hz).

EXAMPLE 3

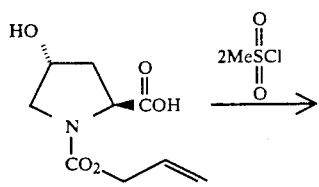

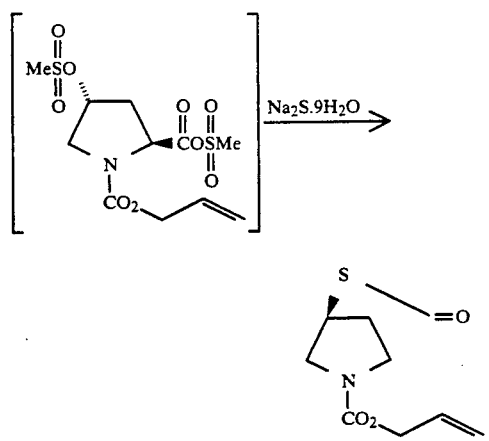

To a solution of (2S,4R)-1-allyloxycarbonyl-4-hydroxy-2-pyrrolidinecarboxylic acid (112 mg) in methylene chloride (1 ml), cooled to −10° C., were added triethylamine (132 mg) and methanesulfonyl chloride (137 mg). The mixture was stirred for 1 hour at −10° C. At this temperature, sodium sulfide 9-hydrate (125 mg) was added thereto. After the temperature was elevated to room temperature, the mixture was stirred overnight. After 1N-hydrochloric acid (1.04 ml) was added, the mixture was diluted with ethyl acetate (10 ml), and dried over magnesium sulfate. Distillation of the solvent, followed by purifying the residue by silica gel chromatography, gate (1S,4S)-5-allyloxycarbonyl-2-thia-5-azabicyclo -8 1.1.1]heptan-3-one.

EXAMPLE 4-(1)

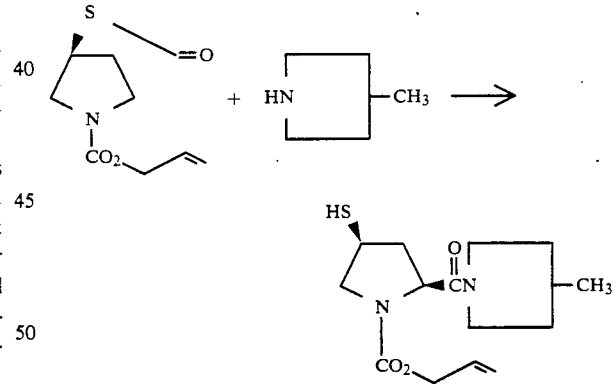

To a solution of (1S,4S)-5-allyloxycarbonyl-2-thia-5-azabicyclo[2.2.1]heptan-3-one (38.5 mg) in tetrahydrofuran (1 ml) was added 4-methylpiperidine (19.7 mg). The mixture was stirred for 4 hours at room temperature. After the reaction was over, 1N-hydrochloric acid (0.036 ml) was added thereto, and the mixture was diluted with ethyl acetate (2 ml) and dried above magnesium sulfate. Distillation of the solvent, followed by purifying the residue by silica gel chromatography, gave oily 1-[(2S,4S) -1-allyloxycarbonyl-4-mercapto-2-pyrrolidinecarbonyl]-4-methylpiperidine.

IR (neat): 2532, 1704, 1652 cm$^{-1}$
NMR(CDCl$_3$) δ0.85–1.45(2H, m), 0.94(3H, d, J=6 Hz), 1.52–1.93(5H, m), 2.50–2.75(2H, m), 3.02(1H, q, J=14 Hz), 3.20(1H, m), 3.38(1H, t, J=10 Hz), 3.81(1H, t, J=11 Hz), 4.09(1H, dt, J=7, 11 Hz), 4.45–4.75(4H, m), 5.10–5.35(2H, m), 5.86(1H, m)

EXAMPLE 4-(2)

Example 4-(1) was repeated except that toluene was used in place of the tetrahydrofuran as solvent, to obtain oily 1-[(2S,4S)-1-allyloxycarbonyl-4-mercapto-2-pyrrolidinecarbonyl]-4-methyl-piperidine.

EXAMPLE 4-(3)

Example 4-(1) was repeated except that ethyl acetate was used in place of the tetrahydrofuran as solvent, to obtain oily 1-[(2S,4S)-1-allyloxycarbonyl-4-mercapto-2-pyrrolidinecarbonyl]-4-methylpiperidine.

EXAMPLE 4-(4)

Example 4-(1) was repeated except that methylene chloride was used in place of the tetrahydrofuran as solvent, to obtain oily 1-[(2S,4S)-1-allyloxycarbonyl-4-mercapto-2-pyrrolidinecarbonyl]-4-methylpiperidine.

EXAMPLE 4-(5)

Example 4-(1) was repeated except that a mixed solvent of ethyl acetate and ethanol (1:1 volume ratio) was used in place of the tetrahydrofuran as solvent, to obtain oily 1-[(2S,4S)-1-allyloxycarbonyl-4-mercapto-2-pyrrolidinecarbonyl]-4-methylpiperidine.

EXAMPLE 4-(6)

Example 4-(1) was repeated except that dimethylformamide was used in place of the tetrahydrofuran as solvent, to obtain oily 1-[(2S,4S)-1-allyloxycarbonyl-4-mercapto-2-pyrrolidinecarbonyl]-4-methylpiperidine.

EXAMPLE 5-(1)

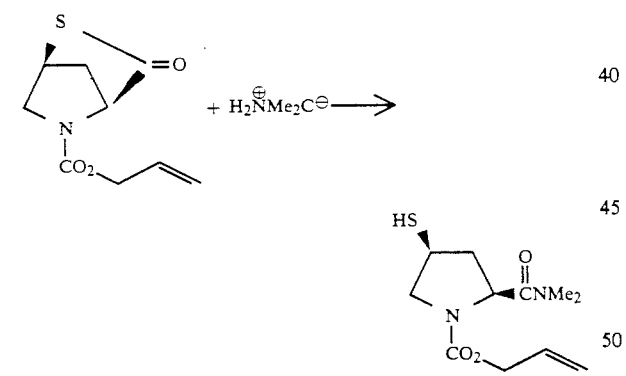

To a solution of (1S,4S)-5-allyloxycarbonyl-2-thia-5-azabicyclo[2.2.1]heptan-3-one (39.2 mg) in acetonitrile (1 ml) were added dimethylamine hydrochloride (16.5 mg) and diisopropylethylamine (35.7 mg). The mixture was stirred for 3 hours at room temperature. After the reaction was over, 1N-hydrochloric acid (0.092 ml) was added thereto, and the mixture was diluted with ethyl acetate (2 ml) and dried over magnesium sulfate. Distillation of the solent, followed by purifying the residue by silica gel chromatography, gave oily (2S,4S) -N,N-dimethyl-1-allyloxycarbonyl-4-mercapto-2-pyrrolidinecarboxamide.

IR (neat): 2534, 1700, 1654 cm$^{-1}$

NMR(CDCl$_3$) δ1.81–1.96(2H, m), 2.69(1H, m), 2.96(3H×⅓, s), 2.98(3H×⅔, s), 3.04(3H×⅓, s), 3.09(3H×⅔, s), 3.23(1H, m), 3.39(1H×⅔, dd, J=10, 11 Hz), 4.06(1H×⅓, dd, J=7, 11 Hz), 4.45–4.72(3H, m), 5.13–5.35(2H, m), 5.86(1H, m).

EXAMPLE 5-(2)

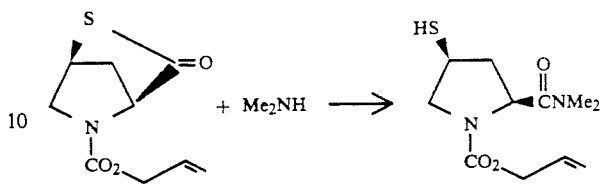

To a solution of (1S,4S)-5-allyloxycarbonyl-2-thia-5-azabicyclo[2.2.1]heptan-3-one (37.3 mg) in tetrahydrofuran (0.3 ml) was added an aqueous 40% dimethylamine solution (39.2 mg). The mixture was stirred for 2 hours at room temperature. After the reaction was over, the same post-treatment as in Example 5-(1) was conducted, thereby to give oily (2S,4S)-N,N-dimethyl-1-allyloxycarbonyl -4-mercapto-2-pirrolidinecarboxamide.

EXAMPLE 6

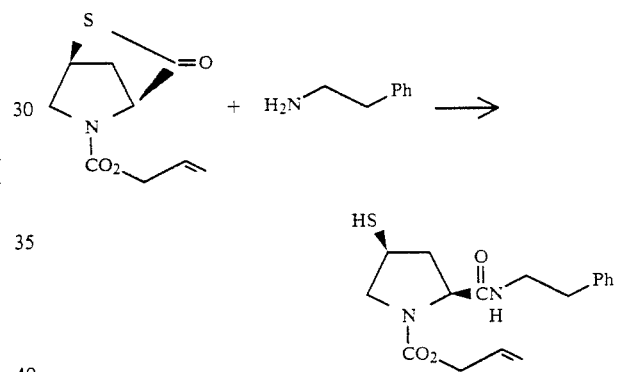

To a solution of (1S,4S)-5-allyloxycarbonyl-2-thia-5-azabicyclo[2.2.1]heptan-3-one (32.2 mg) in tetrahydrofuran (1 ml) was added 2-phenylethylamine (20.1 mg). The mixture was stirred for 4 hours at room temperature. After the reaction was over, 1N-hydrochloric acid (0.027 ml) was added thereto, and the mixture was diluted with ethyl acetate (2 ml) and dried over magnesium sulfate. Distillation of the solvent, followed by purifying the residue by silica gel chromatography, gave oily (2S,4S) -N-(2-phenylethyl)-1-allyloxycarbonyl-4-mercapto-2-pyrrolidinecarboxamide.

IR (neat): 3306, 2542, 1708, 1665 cm$^{-1}$

NMR(CDCl$_3$) δ2.24(1H, m), 2.58(1H, m), 2.81(2H, t, J=7 Hz), 3.16–3.35(2H, m), 3.45–3.63(2H, m), 4.00(1H, br), 4.26(1H, dd, J=7, 8 Hz), 4.54(2H, d, J=5 Hz), 5.17–5.35(1H, m), 5.87(1H, m), 7.15–7.34(5H, m).

EXAMPLE 7

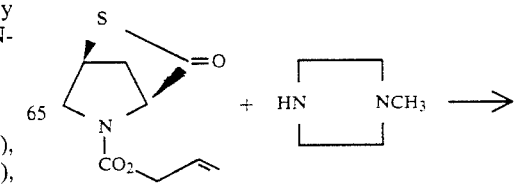

-continued

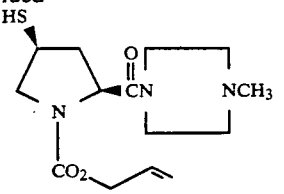

To a solution of (1S,4S)-5-allyloxycarbonyl-2-thia-5-azabicyclo[2.2.1]heptan-3-one (30.6 mg) in tetrahydrofuran (1 ml) was added 4-methylpiperazine (15.8 mg). The mixture was stirred for 33 hours at room temperature. After the reaction was over, the mixture was diluted with ethyl acetate (2 ml). Distillation of the solvent gave oily 1-[(2S,4S)-1-allyloxycarbonyl-4-mercapto-2-pyrrolidinecarbonyl]-4-methylpiperazine.

IR (neat): 2534, 1700, 1653 cm$^{-1}$

NMR(CDCl$_3$) δ1.83(2H, m), 2.08-2.53(4H, m), 2.27(3H, s), 2.65(1H, m), 3.21(1H, br), 3.35(1H, t, J=10 Hz), 3.39-3.68(4H, m), 4.04(1H, m), 4.42-4.68(3H, m), 5.09-5.32(2H, m), 5.83 (1H, m).

EXAMPLE 8

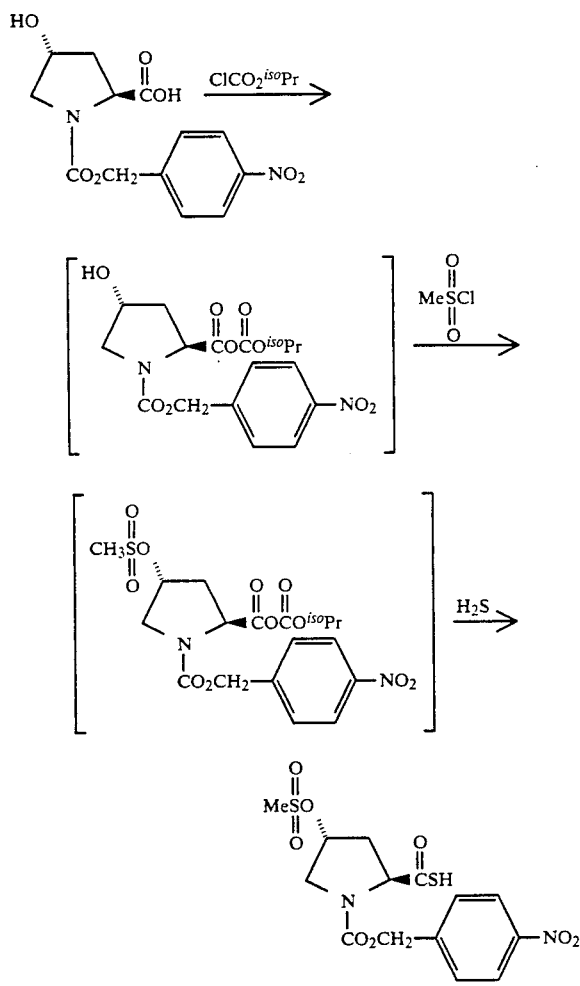

A solution of (2S,4R)-1-p-nitrobenzyloxycarbonyl-4-hydroxy-2-pyrrolidinecarboxylic acid (apparently 3.33 g, containing about 6% water) in methylene chloride (100 g) was subjected to azeotropic distillation for dehydration under room pressure to concentrate to about 30 g. Triethylamine (1.21 g) was added thereto, and the mixture was cooled to −15° C. Isopropyl chlorocarbonate (1.35 g) was added thereto, and the mixture was stirred for 30 minutes at the same temperature. Then, triethylamine (1.62 g) and methanesulfonyl chloride (1.6 g) were added thereto, and the mixture was stirred for 30 minutes at the same temperature. After triethylamine (2.53 g) was added, an excessive amount of hydrogen sulfide was passed through for 30 minutes. After aqueous 1 mole/1 hydrochloric acid solution (40 ml) was added, the mixture was diluted with methylene chloride (20 ml) for extraction. After washing was made with aqueous 1 mole/1 hydrochloric acid solution (40 ml), organic layer was dried over magnesium sulfate. Distillation of the solvent gave oily crude (2S,4R)-1-p-nitrobenzyloxycarbonyl-4-methanesulfonyloxy -2-pyrrolidinethiocarboxylic acid (4.0 g), which was used for the next reaction without further purification.

IR (neat): 1700, 1522, 1347, 1174 cm$^{-1}$

NMR(CDCl$_3$) δ2.31-2.41(1H, m), 2.61-2.83(1H, m), 3.06(3H, m), 3.76-3.84(1H, m), 4.03-4.15 (1H, m), 4.58-4.70(1H, m), 5.16-5.39(3H, m), 7.52(2H, pseudo t, J=8.6 Hz), 8.23(2H, d, J=8.6 Hz).

EXAMPLE 9

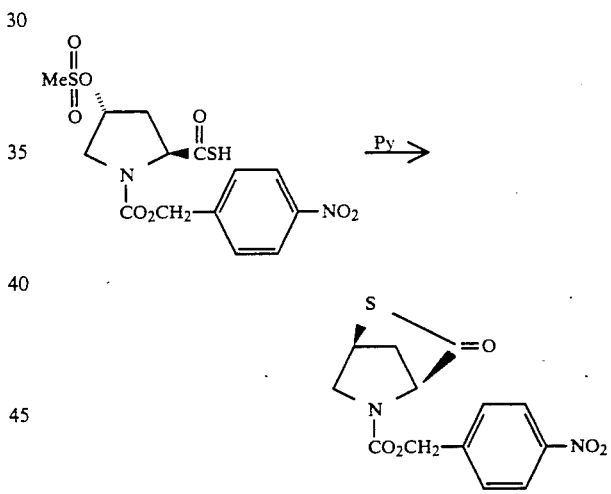

To a solution of crude (2S,4R)-1-p-nitrobenzyloxycarbonyl -4-methanesulfonyloxy-2-pyrrolidinethiocarboxylic acid (4.0 g) obtained in Example 8 in methylene chloride (40 ml) was added pyridine (1.91 g). The mixture was heated under refluxing for 7 hours. After the reaction was over, the mixture was washed with aqueous 1 mole/1 hydrochloric acid solution. The organic layer was dried over magnesium sulfate. After the solvent was distilled, residue was purified by silica gel chromatography to give (1S,4S)-5-p-nitrobenzyloxycarbonyl-2-thia-5-azabicyclo-[2.2.1]heptan-3-one.

m.p.: 103°-104° C.

IR (neat): 1747, 1704, 1518, 1351 cm$^{-1}$.

NMR(CDCl$_3$) δ2.11-2.27(2H, m), 3.67-3.72(1H, m), 3.85-3.90(1H, m), 4.15-4.19(1H, m), 4.62-4.70(1H, m), 5.21(1H, d, J=13.7 Hz), 5.31(1H, d, J=13.7 Hz), 7.54(2H, d J=8.6 Hz), 8.23(2H, d, J=8.6 Hz).

EXAMPLE 10

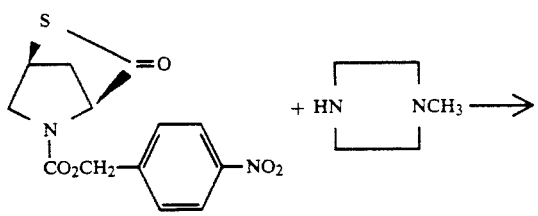

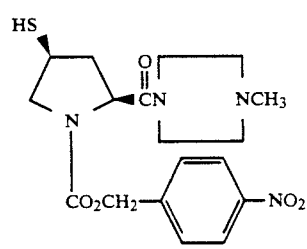

To a solution of (1S,4S)-5-p-nitrobenzyloxycarbonyl-2-thia-5-azabicyclo[2.2.1]heptan-3-one (308 mg) in methylene chloride (2.0 g) was added N-methylpiperazine (105 mg). The mixture was stirred for 7 hours at room temperatures. After the reaction was over, the solvent was distilled to give solid 1-[(2S,4S)-1-p-nitrobenzyloxycarbonyl-4-mercapto-2-pyrrolidinecarbonyl]-4-methylpiperazine.

m.p.: 129°–130 ° C.

IR (neat); 1711, 1657, 1524, 1345 cm$^{-1}$

NMR(CDCl$_3$) δ4.05–4.18(1H, m), 4.60–4.75(1H, m), 5.01–5.35(2H, m), 7.44(2H×½, d, J=8.6 Hz), 7.51(2H×½, d, J=8.6 Hz), 8.19(2H×½, d, J=8.6 Hz), 8.21(2H×½, d, J=8.6 Hz).

REFERENCE EXAMPLE 1

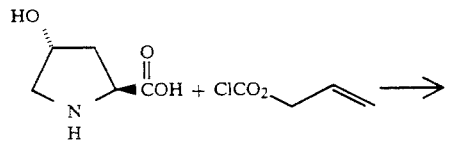

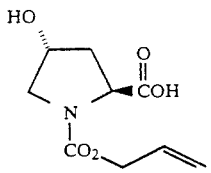

To a solution of trans-4-hydroxy-L-proline (35.9 g) and sodium hydroxide (23.9 g) in water (330 ml) was added dropwise a solution of allyl chlorocarbonate (36.3 g) in methylene chloride (250 ml) under ice-cooling, and stirring was continued for 2 hours. Aqueous layer was separated from the reaction mixture, washed twice each with methylene chloride (100 ml), and then acidified by adding concentrated sulfuric acid (25 g) dropwise at a temperature below 30° C. After adding table salt (120 g), the mixture was extracted twice each with ethyl acetate (220 ml). Extract was dried over magnesium sulfate. Distillation of the solvent gave crude crystalline trans-1-allyloxycarbonyl-4-hydroxy-L-proline (62 g). Purification of the crude crystals by repulping with toluene gave trans-1-allyloxycarbonyl-4-hydroxyl-L-proline (56.1 g) having m.p. 93–°94° C.

IR(Nujol): 3330, 1740, 1675, 1645 cm$^{-1}$

What we claim is:

1. A pyrrolidine derivative represented by the formula (1):

(1)

wherein R means a protective group for the amino group selected from the group consisting of substituted and unsubstituted C$_{1-6}$ lower alkoxycarbonyl groups; substituted and unsubstituted C$_{2-6}$ lower alkenyloxycarbonyl groups; substituted and unsubstituted benzyloxycarbonyl groups; substituted and unsubstituted benzyl groups; substituted and unsubstituted trialkylsilyl groups; substituted and unsubstituted dialkylarylsilyl groups; substituted and unsubstituted alkyldiarylsilyl groups; substituted and unsubstituted triarylsilyl groups; wherein the substituents are selected from the group consisting of one or more C$_{1-4}$ lower alkyl groups, C$_{1-4}$ lower alkoxy groups, aryl groups, halogen atoms and nitro groups.

2. A pyrrolidine derivative according to claim 1 wherein R is a substituted or unsubstituted C$_{2-6}$ lower alkenyloxycarbonyl group or a substituted or unsubstituted benzyloxycarbonyl group, wherein the substituents are selected from the group consisting of one or more C$_{1-4}$ lower alkyl groups, C$_{1-4}$ lower alkoxy groups, aryl groups, halogen atoms and nitro groups.

3. A pyrrolidine derivative according to claim 2 wherein R is an allyloxycarbonyl group.

4. A pyrrolidine derivative according to claim 2 wherein R is a p-nitrobenzyloxycarbonyl group.

5. A process for preparing pyrrolidine derivatives represented by the formula (1):

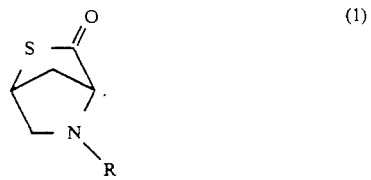

(1)

wherein R means a protective group for the amino group, comprising (A) allowing a compound represented by the formula (2)

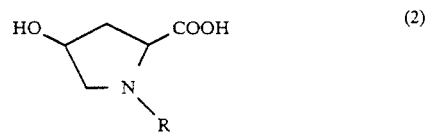

(2)

wherein R has the same meaning as above, to react with active esterifying agents in the presence of a base, and then with hydrogen sulfide in the presence of a base, to give a compound represented by the formula (3):

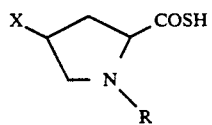 (3)
wherein R has the same meaning as above and X means an active ester of a hydroxyl group, and further treating the compound of the formula (3) with a base, or (B) allowing the compound represented by the formula (2) mentioned above to react with active esterifying agents in the presence of a base, and then with an alkali metal salt of hydrogen sulfide.
* * * * *